(12) United States Patent
Nee et al.

(10) Patent No.: US 9,067,203 B2
(45) Date of Patent: Jun. 30, 2015

(54) INTEGRATED SPECIMEN CUP SYSTEM FOR TAMPERPROOF SAMPLE TESTING AND SECURE RETENTION

(71) Applicant: uVera Diagnostics, Inc., Norfolk, VA (US)

(72) Inventors: Richard M Nee, Virginia Beach, VA (US); William D Nee, Virginia Beach, VA (US)

(73) Assignee: UVERA DIAGNOSTICS, INC., Norfolk, VA (US)

( * ) Notice: Subject to any disclaimer, the term of this patent is extended or adjusted under 35 U.S.C. 154(b) by 0 days.

(21) Appl. No.: 14/059,485

(22) Filed: Oct. 22, 2013

(65) Prior Publication Data

US 2014/0112844 A1  Apr. 24, 2014

Related U.S. Application Data

(60) Provisional application No. 61/717,291, filed on Oct. 23, 2012.

(51) Int. Cl.
*B01L 3/00* (2006.01)
*A61B 10/00* (2006.01)

(52) U.S. Cl.
CPC ......... *B01L 3/502* (2013.01); *B01L 2200/0689* (2013.01); *B01L 2200/141* (2013.01); *B01L 2300/043* (2013.01); *B01L 2300/0663* (2013.01); *B01L 2400/0644* (2013.01); *A61B 10/0045* (2013.01); *A61B 10/0096* (2013.01)

(58) Field of Classification Search
CPC ............ B01L 3/502; B01L 2200/0689; B01L 2200/141
USPC .................................. 422/401, 402, 68.1, 557
See application file for complete search history.

(56) References Cited

U.S. PATENT DOCUMENTS

| 6,277,646 | B1 * | 8/2001 | Guirguis et al. | 436/165 |
| 6,575,193 | B2 * | 6/2003 | Chang et al. | 137/558 |
| 7,927,560 | B2 * | 4/2011 | Richard | 422/401 |
| 2003/0022392 | A1 * | 1/2003 | Hudak | 436/518 |
| 2003/0099572 | A1 * | 5/2003 | Ng et al. | 422/58 |
| 2006/0029517 | A1 * | 2/2006 | Hartselle | 422/61 |

FOREIGN PATENT DOCUMENTS

WO   WO2011156912   * 12/2011

* cited by examiner

*Primary Examiner* — Sam P Siefke
(74) *Attorney, Agent, or Firm* — Peter J. Van Bergen (57) ABSTRACT

A specimen cup system includes a cup defining first and second reservoirs in fluid communication with one another. The first reservoir has an open top with spaced-apart upper and lower annular flanges defined at the open top's external periphery. A test card is permanently disposed in the second reservoir. A base, rotatably coupled to the cup, defines a chamber having an opening therein. The opening of the chamber is in fluid communication only with the first reservoir when the base is in a first position, and is in fluid communication only with the second reservoir when the base is in a second position. A seal, rim, and lid cooperate with the upper and lower annular flanges of the open top of the first reservoir to seal the first reservoir after a specimen has been deposited therein.

12 Claims, 7 Drawing Sheets

INTEGRATED SPECIMEN CUP SYSTEM FOR TAMPERPROOF SAMPLE TESTING AND SECURE RETENTION

Pursuant to 35 U.S.C. §119, the benefit of priority from provisional application 61/717,291, with a filing date of Oct. 23, 2012, is claimed for this non-provisional application.

FIELD OF THE INVENTION

The invention relates generally to testing of body-fluid samples, and more particularly to an integrated specimen cup system that provides for sample testing and secure retention of a portion of the sample in a tamperproof container for improved confidence in test results.

BACKGROUND OF THE INVENTION

Body-fluid-based drug testing has become pervasive in our modern society. From government and industry workers to amateur and professional athletes, most people will be subjected to at least one drug test at some point in their life. Accordingly, it is imperative that the drug testing industry provide drug testing systems that guarantee a body-fluid sample will remain contaminant-free before, during and after a drug test, and provide a high degree of confidence in the test results.

In general, drug testing "systems" utilize some type of specimen cup that a user fills or partially fills with a body-fluid sample. Recently, a variety of specimen cups have included the means to have a drug test card inserted therein where the card is exposed to the body-fluid sample and subsequently provides an indication about the presence/absence of one or more substances of interest. However, to date, no drug testing specimen cup exists that provides for collection of a body-fluid sample, testing of a portion of the sample, the guaranteed secure retention of the remainder of the sample in a contaminant-free sealed environment, and a system that remains tamperproof from manufacturing through the entire testing process so that test subjects and testing authorities have a high degree of confidence in the test results.

SUMMARY OF THE INVENTION

Accordingly, it is an object of the present invention to provide a specimen cup system for drug testing.

Another object of the present invention is to provide an integrated specimen cup system that can be used to collect a body-fluid sample and test a portion of the sample while retaining a remainder of the sample in a tamperproof and contaminant-free environment.

Other objects and advantages of the present invention will become more obvious hereinafter in the specification and drawings.

In accordance with the present invention, a specimen cup system for sample testing includes a cup defining a first reservoir and a second reservoir in fluid communication with one another at a lower portion of the cup. The first reservoir has an open top, and has an upper annular flange and a lower annular flange defined at an external periphery of the open top. The upper annular flange and lower annular flange are spaced apart from one another. The second reservoir is sealed except for being in fluid communication with the first reservoir. A specimen test card is permanently disposed in the second reservoir. A base is rotatably coupled to the lower portion of the cup. The base defines a chamber having an opening therein. The base is rotatable from a first position to a second position relative to the cup. The opening of the chamber is in fluid communication only with the first reservoir when the base is in the first position. The opening of the chamber is in fluid communication only with the second reservoir when the base is in the second position. The base and cup are locked together to prevent relative rotation when the base is in the second position. A flexible seal is fitted over the open top of the first reservoir such that the upper annular flange and lower annular flange remain exposed. An open rim, fitted over the seal, has tabs captured between the upper annular flange and lower annular flange so that the seal is captured between the open top and the rim. An annular portion of the seal is exposed inside of the open top. A solid lid, hingedly coupled to the rim, includes an annular wall extending therefrom and sized to pass through the rim to sealingly engage the annular portion of the seal when the lid is hingedly positioned to be fully engaged with the rim.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
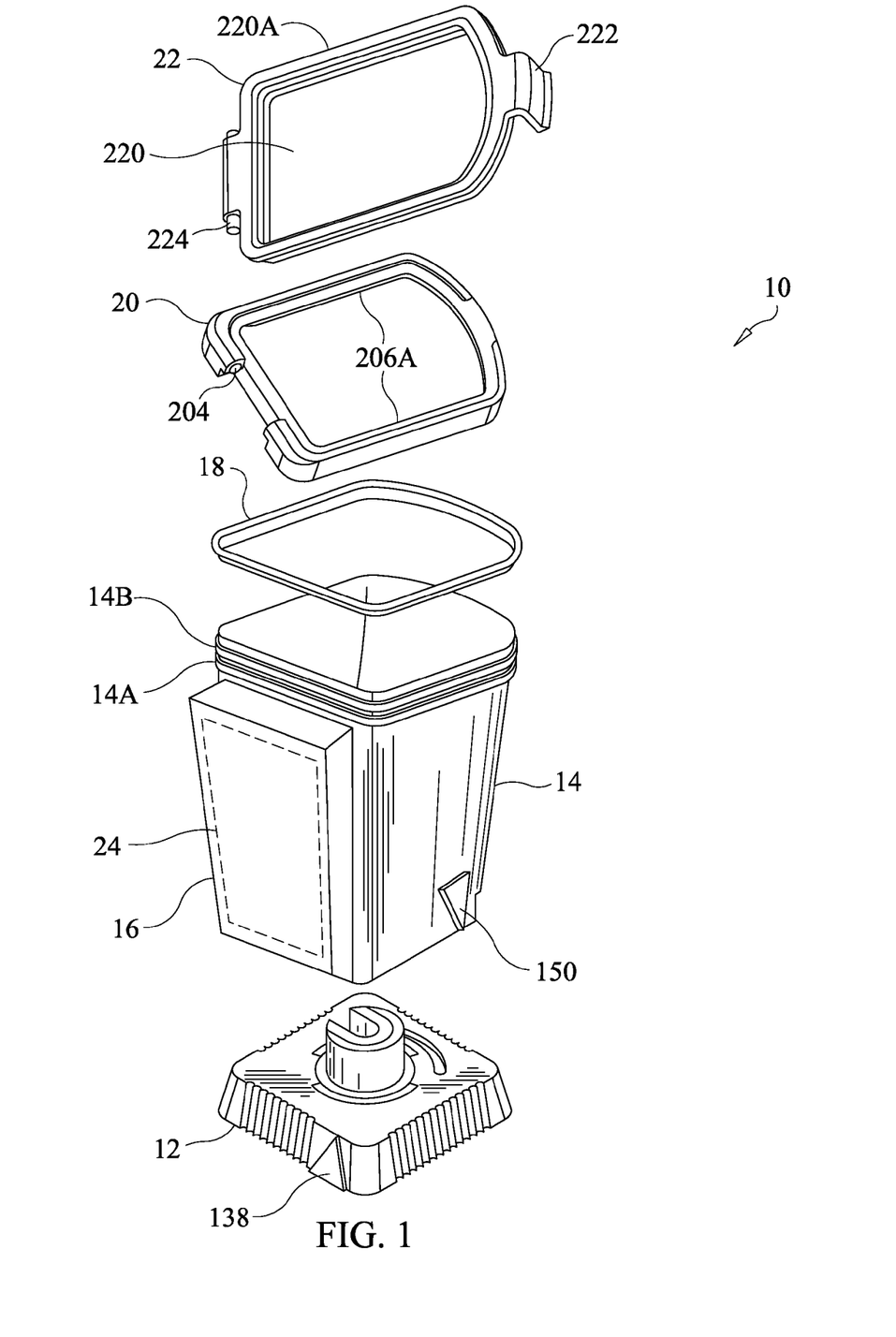
FIG. 1 is an exploded perspective view of an integrated specimen cup system in accordance with an embodiment of the present invention with the system in its pre-test position.
Figure 2:
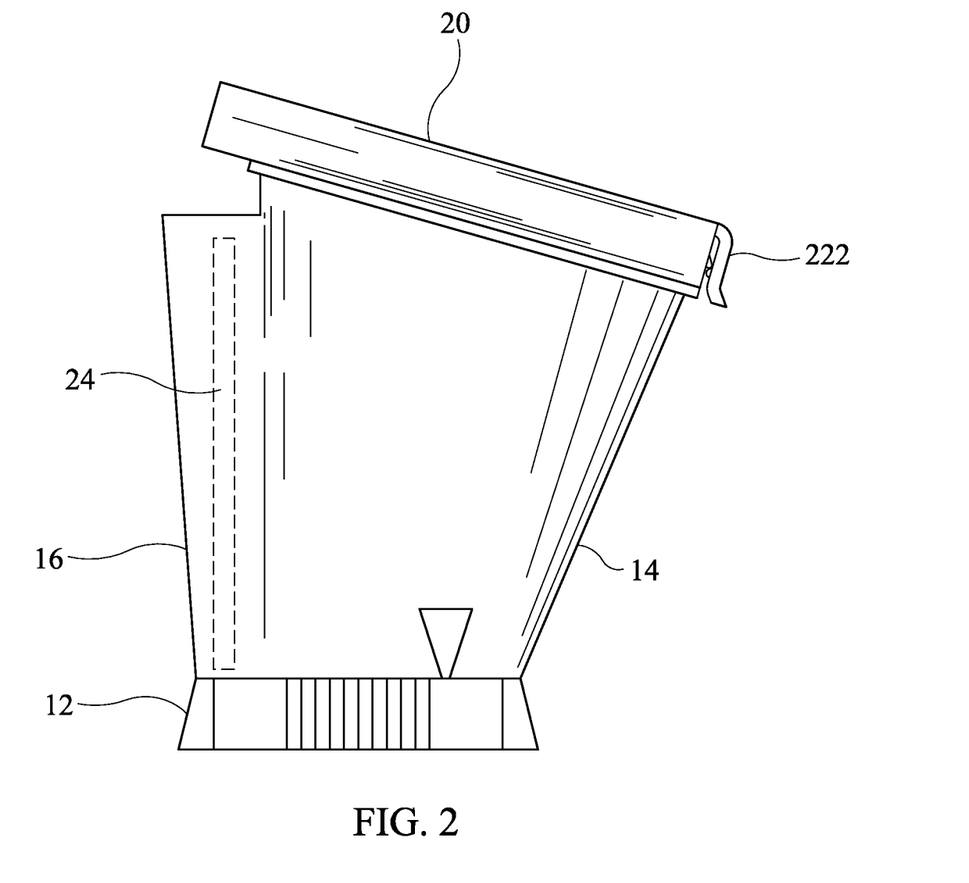
FIG. 2 is a side view of an assembled/sealed integrated specimen cup system in its pre-test position.

Referring now to the drawings and more particularly to FIGS. 1 and 2, an integrated specimen cup system in accordance with an embodiment of the present invention is shown and is referenced generally by numeral 10. In general, specimen cup system 10 can be used to collect, test, and retain body-fluids (e.g., urine, blood, saliva, semen, etc.) deposited therein in a sealed fashion. As will be explained further herein, specimen cup system 10 seals the body-fluid therein prior to the testing thereof, provides for in-situ and on-demand drug testing of a portion of the body-fluid, and securely retains a remainder of the body-fluid in a sealed contaminant-free environment. Several of the features of specimen cup system 10 are described in U.S. Pat. No. 7,927,560, the contents of which are hereby incorporated by reference. However, for a complete description of the present invention, these features will also be described herein. In addition, specimen cup system 10 possesses several new features that improve upon the above-referenced patent. Briefly, the new features of the present invention make the system more "user friendly", provide an improved sealing arrangement for secure sample retention, and provide a tamperproof system from manufacturing through testing.

Prior to describing specimen cup system 10 in detail, the basic parts of the illustrated embodiment of system 10 are defined generally as follows:
 a base 12,
 a sample cup 14 rotatably coupled to base 12,
 a sealed test card support 16 integrated with sample cup 14,
 a flexible annular seal 18 fitted on the open top of sample cup 14,
 a sample cup rim 20 attachable to the open top of sample cup 14 with annular seal 18 captured therebetween,
 a sample cup lid 22 hingedly coupled to rim 20 and sealed against/within annular seal 18 when lid 22 is closed over the top of sample cup 14 as shown in FIG. 2, and
 a specimen test card 24 fitted within sealed test card support 16.

The above terms will be used throughout the remainder of the description when referring to these parts of system 10.

Figure 3:
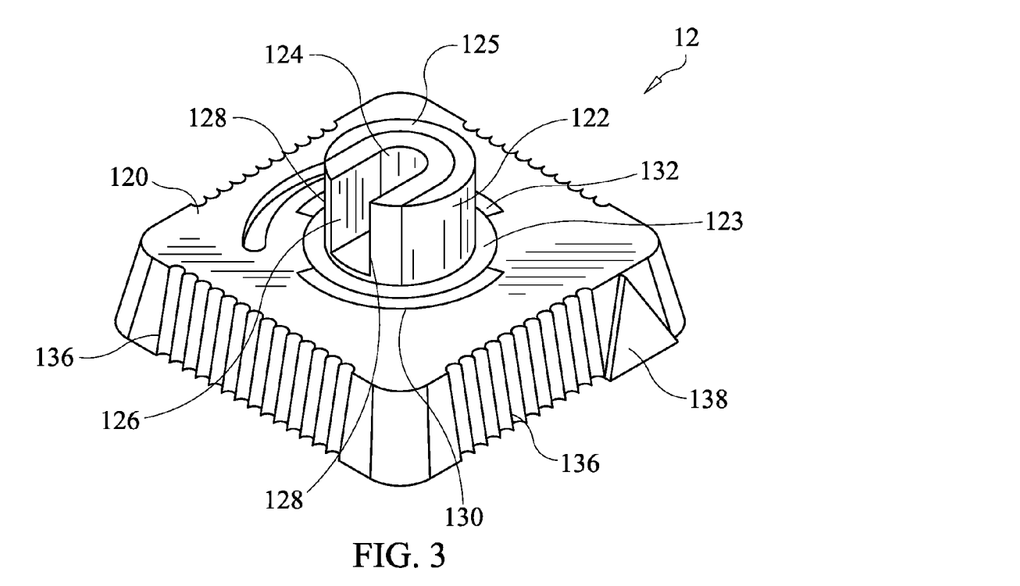
FIG. 3 is an isolated perspective view of the specimen cup system's base.
Figure 4:
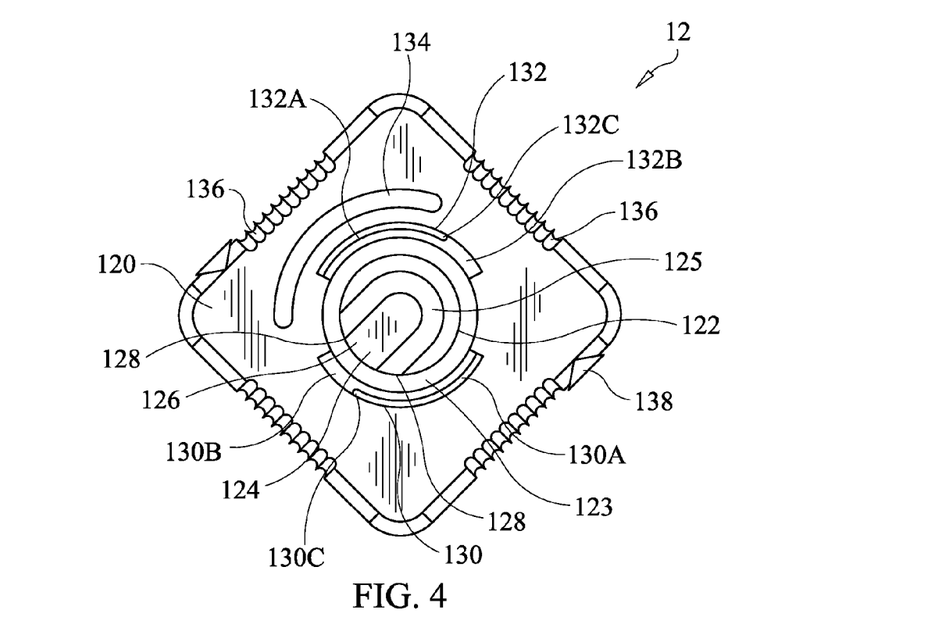
FIG. 4 is a top view of the base.

Referring additionally now to FIGS. 3 and 4, base 12 will be described in greater detail. Base 12 has a support block 120 that can be sized/shaped to match the bottom of sample cup 14. Extending vertically upward from support block 120 is a hollow post 122. In the illustrated embodiment, support block 120 and post 122 are integrally formed (e.g., by injection molding) with a recessed annular channel 123 surrounding post 122. Annular channel 123 cooperates with a corresponding receptacle extension portion of sample cup 14 as will be explained later herein.

The hollow portion of post 122 defines a chamber 124 having a selected volume for the collection of a portion of a body-fluid sample as will be explained later below. Chamber 124 is accessed via an opening 126 in a radial wall of post 122. Opening 126 begins where post 122 and support block 120 meet and can extend up to the full height of post 122 as illustrated. The top of chamber 124 can be open (as shown) or closed without departing from the scope of the present invention. Opening 126 is framed by edges 128 that define a fluid-tight seal with the inside walls of a post housing or receptacle (not shown) formed in sample cup 14 as will be described later below. Note that if the top of chamber 124 is open, the top edges 125 thereof must also define a fluid-tight seal with the inside top portion of the above-mentioned post receptacle.

Three curved slots are formed in support block 120. The first two slots 130 and 132 can be (but need not be) cut all the way through support block 120 and are formed on diametrically-opposing sides of post 122 as best seen in FIG. 4. Each of slots 130 and 132 has a respective smaller width region 130A and 132A and a respective wider width region 130B and 132B such that respective lips 130C and 132C are formed at the interface of respective regions 130A/130B and 132A/132B. Wider width regions 130B and 132B essentially define notches that are diametrically-opposed to one another. The rotational angle defined by the length of slots 130 and 132 define the amount of rotational travel of base 12 relative to sample cup 14. For example, in the illustrated embodiment, the length of slots 130 and 132 will define approximately 90° of rotation of base 12.

The third curved slot formed in support block 120 is a curved indexing slot 134 used to assure the proper positioning of base 12 relative to sample cup 14 during the assembly of base 12 to sample cup 14. Slot 134 can be cut partially into or all the way through support block 120. The rotational angle defined by the length of indexing slot 134 should be equal to or greater than that of slots 130 and 132.

To facilitate the gripping of base 12, some type of grip enhancement such as knurled edges 136 can be formed about some or all of the perimeter of support block 120. One or more positioning indicia 138 (e.g., marks, words, etc.) can also be provided (e.g., molded in, printed or painted on, attached to, etc.) on the perimeter of support block 120. Briefly, positioning indicia 138 are used to identify that specimen cup system 10 is in its pre-test or test position as will be described later below. It is to be understood that the present invention is not limited to this particular construction of base 12 as other constructions of base 12 could be utilized without departing from the scope of the present invention.

Referring additionally now to FIGS. 5-8, sample cup 14 will be described in greater detail. For clarity, sample cup 14 in FIGS. 5-8 is illustrated without base 12 coupled thereto. In general, sample cup 14 defines two reservoirs or chambers 140 and 142 that, absent the presence of base 12, are in constant fluid communication with one another in the lower regions thereof. However, when base 12 is coupled to sample cup 14 in its pre-test position, fluid communication between chambers 140 and 142 is prohibited as will be explained further below. Chambers 140 and 142 defined by sample cup 14 are also referred to herein as a larger specimen cup 140 and a smaller test cup 142 that is formed adjacent to the bottom of one side of specimen cup 140. In the illustrated embodiment, cups 140 and 142 are integrated portions of sample cup 14 that are formed during the manufacture of sample cup 14. Sample cup 14 will typically be made from a transparent material to make test card 24 visible in test card support 16, and to clearly indicate that a body-fluid sample (not shown) is in contact with the lower portion of test card 24 that will extend into test cup 142 as will be explained further below.

Figure 6:
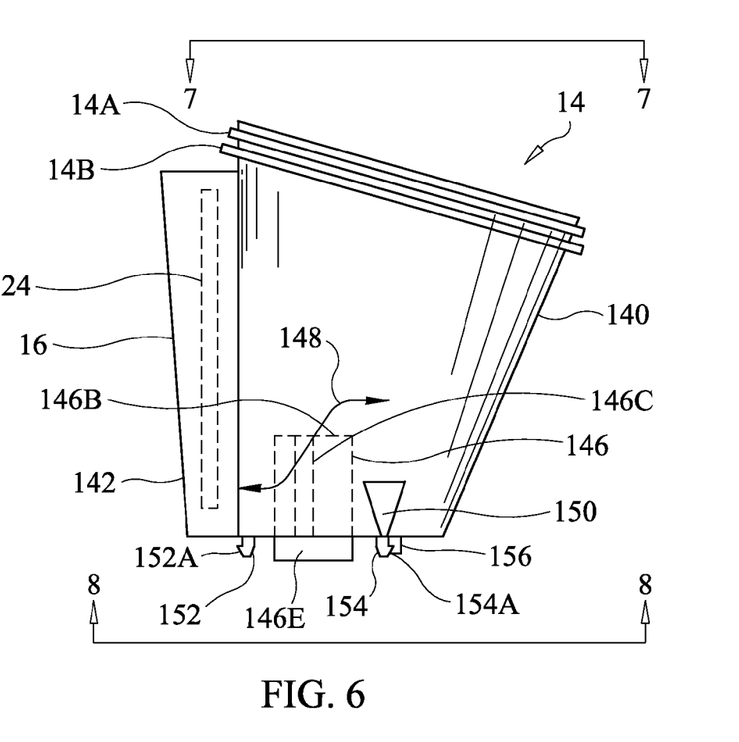
FIG. 6 is a side view of the sample cup.
Figure 7:
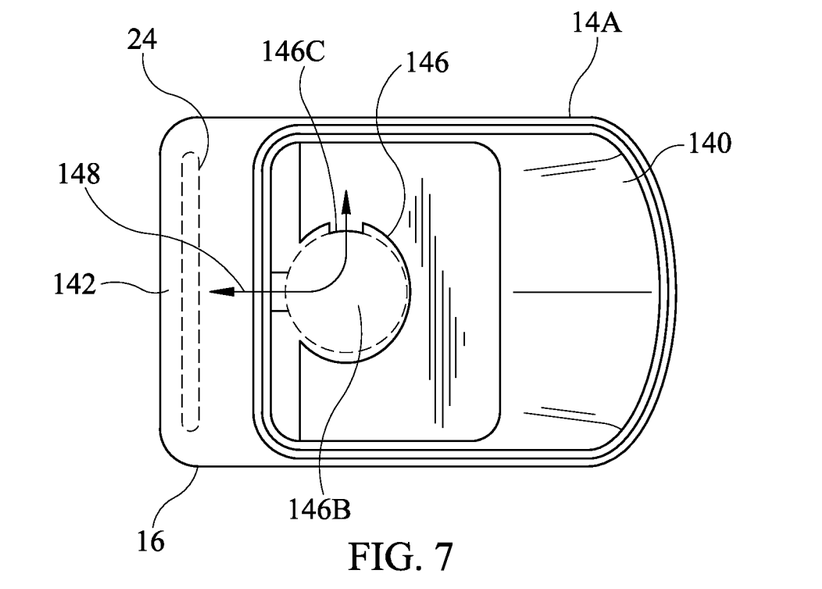
FIG. 7 is a top view of the sample cup taken along line 7-7 in FIG. 6.

Specimen cup 140 is open at the top thereof where spaced-apart annular upper and lower flanges 14A and 14B are formed/defined around the outside periphery thereof. Flanges 14A and 14B cooperate with seal 18, rim 20 and lid 22 (FIGS. 1 and 2) to seal specimen cup 140. The particular design and cooperation between seal 18, rim 20, lid 22, and flanges 14A/14B will be described later herein. The top of specimen cup 140 is pitched downward at an angle a as best seen in FIG. 6 to facilitate the filling thereof with urine by a female user. Angle a can range from approximately 10° to approximately 20° with approximately 15° being typical.

Formed on the inside of specimen cup 140 at the bottom thereof is a hollow post housing or receptacle 146 having an open bottom 146A (FIG. 8), a closed top 146B (FIG. 7), and first and second openings 146C and 146D formed in radial sides thereof. First opening 146C defines an opening between specimen cup 140 and the interior of post receptacle 146. Second opening 146D defines an opening between test cup 142 and the interior of post receptacle 146. The angular spacing between openings 146C and 146D matches the rotation angle defined by slots 130 and 132 in base 12 as described above. Thus, in the illustrated example, openings 146C and 146D are angularly spaced by approximately 90°. Openings 146C and 146D should be defined at least at the lower portion of post receptacle 146 and can extend for the full height of post receptacle 146 as illustrated. Without base 12 coupled to specimen cup 140, the interior of specimen cup 140 is in fluid communication with the interior of test cup 142 via post receptacle 146 and openings 146C/146D formed therein. This fluid communication is indicated in the various views by two-headed arrow 148. A substantially annular receptacle extension 146E protrudes from the bottom of sample cup 14 and is sized to engage annular channel 123 (FIGS. 3-4) of base 12 when specimen cup system 10 is assembled. An o-ring (not shown) can be placed on receptacle extension 146E for sealing engagement with annular channel 123.

Figure 5:
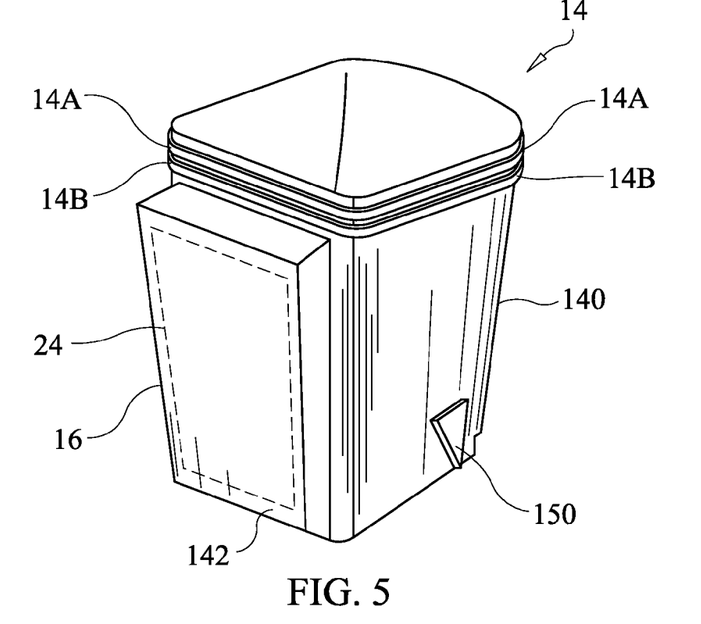
FIG. 5 is an isolated perspective view of an embodiment of the specimen cup system's sample cup.

The outside walls of test cup 142 are essentially defined by the lower region of sealed test card support 16 housing test card 24. That is, test card support 16 (with test card 24 fitted therein) is integrated with and sealed to an outside wall of specimen cup 140 to thereby create test cup 142. The type of test card 24 and the tests it provides are not limitations of the present invention. The exposed test strip(s) (not shown) at the bottom of test card 24 reside in test cup 142 with the remaining portion of test card 24 extending up into test card support 16. To enhance security and bolster test confidence, the placement of test card 24 in test card support 16 and the integration/sealing of support 16 to specimen cup 140 are performed during the manufacture of specimen cup system 10. For example, sample cup 14 and test card support 16 could be manufactured simultaneously such that specimen cup 140 and test cup 142 are open at the bottom of sample cup 14. In this case, test card 24 could be inserted into test card support 16 from (open) test cup 142, and the bottom portion of sample cup 14 could be a separate piece welded in place after test card 24 is positioned in test card support 16. This would effectively seal test card 24 in place permanently, seal test cup 142, and seal the bottom of specimen cup 140. Note that openings 146C/146D in post receptacle 146 are substantially smaller in dimensions than the dimensions of test card 24. Accordingly, once test card support 16 with test card 24 therein are integrated with specimen cup 140, test card 24 is a permanent part of specimen cup system 10 as it cannot be touched, removed, altered, or otherwise tampered with thereby assuring that the test card 24 selected for testing is the one used in a particular test and the one that will always be present in test card support 16.

Provided on the lower outside portion of specimen cup 140 is one or more positioning indicia 150. The relative positions of positioning indicia 138 (on base 12) and positioning indicia 150 (on sample cup 140) are used to identify when specimen cup system 10 is in its pre-test or test position. For example, the relative (e.g., non-aligned) positions of indicia 138 and 150 shown in FIG. 1 could indicate a pre-test position of system 10. Positioning indicia 150 can be molded into specimen cup 140 or applied thereto by any of a variety of methods.

Figure 8:
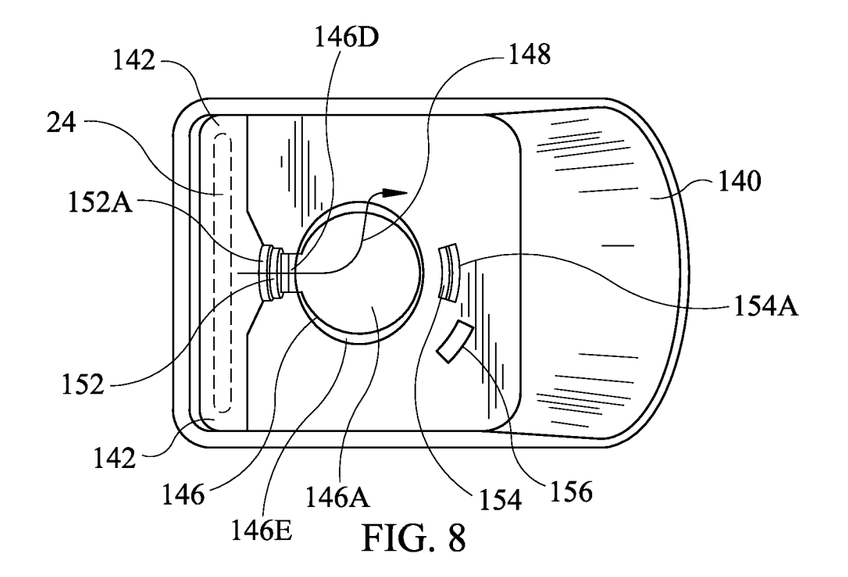
FIG. 8 is a bottom view of the sample cup taken along line 8-8 in FIG. 6.

Affixed to (or integral with) and extending downward from the bottom of specimen cup 140 are three tabs 152, 154, and 156. Tabs 152 and 154 are diametrically disposed about the open bottom 146A of post receptacle extension 146E as best seen in FIG. 8. Each of tabs 152 and 154 has a lip 152A and 154A, respectively, formed at the outboard ends thereof. Tabs 152 and 154 are biased away from one another. To understand the assembly of base 12 to sample cup 14, simultaneous reference will be made to FIGS. 4, 6 and 8. When base 12 is assembled to the bottom of sample cup 14, tabs 152 and 154 respectively engage slots 130 and 132 of base 12. The outward bias of tabs 152 and 154 allows lips 152A and 154A, respectively, to lock onto the underside of support block 120 after tabs 152 and 154 have been pushed through slots 130 and 132. When base 12 is rotated to its test position as will be explained further below, the outward bias of tabs 152 and 154 also allows the tabs to spring radially outward into respective wider width regions 130B and 132B when the tabs are aligned therewith. Once tabs 152 and 154 are engaged in these wider width regions, respective lips 130C and 132C lock tabs 152 and 154 in that portion of slots 130 and 132 to thereby prevent any further relative rotation between base 12 and cup 14. Tab 156 is an indexing tab that will engage indexing slot 134 when base 12 is assembled to the bottom of sample cup 14. Note that the present invention could also be practiced by configuring sample cup 14 with the above-described arrangement of slots and configuring base 12 with the corresponding arrangement of tabs.

Figure 10:
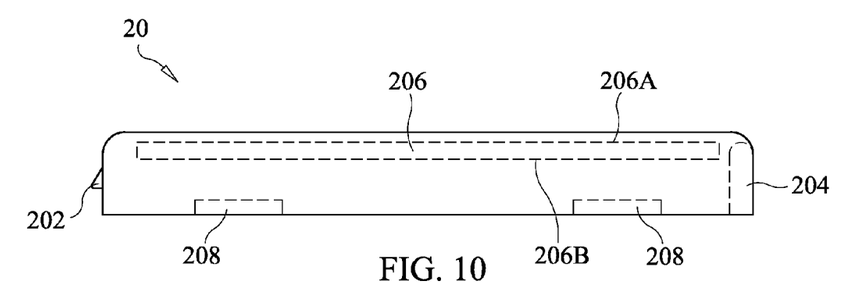
FIG. 10 is a side view of the specimen cup system's rim in accordance with the system embodiment illustrated in FIG. 1.
Figure 11:
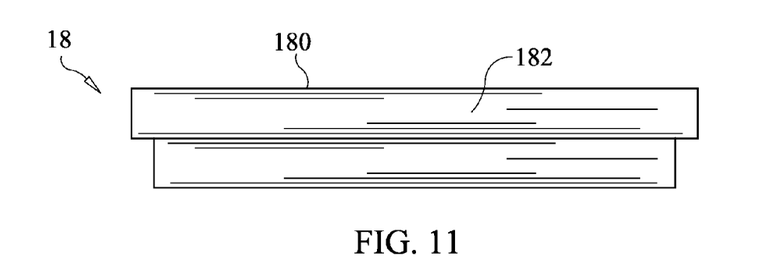
FIG. 11 is a side view of the specimen cup system's annular seal in accordance with the system embodiment illustrated in FIG. 1.
Figure 12:
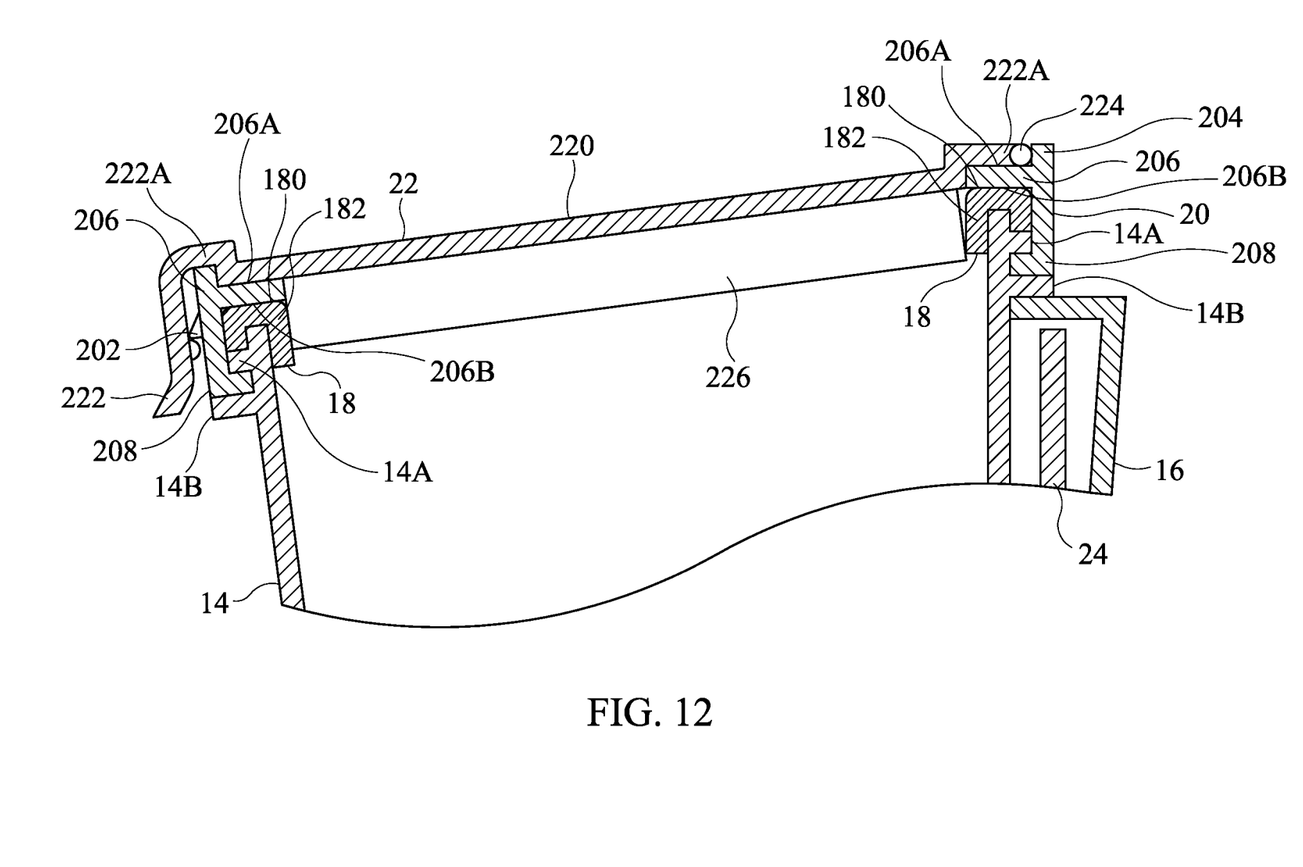
FIG. 12 is a cross-sectional view of the specimen cup system's top region illustrating the relationships between the top of the sample cup, the annular seal, the rim, and the lid in accordance with an embodiment of the present invention.

Referring additionally and simultaneously to FIGS. 9-12, lid 22 (FIG. 9), rim 20 (FIG. 10) and annular seal 18 (FIG. 11) are illustrated in isolated side views, and as they cooperate with one another and the top of sample cup 14 in the cross-sectional view presented in FIG. 12. Lid 22 is a monolithic rigid structure defining a solid top 220 having an annular rim region 220A with a locking tab 222 formed at the front thereof and a hinge pin 224 formed at the back thereof. An annular wall 226 extends away from and within the confines of annular rim region 220A.

Figure 9:
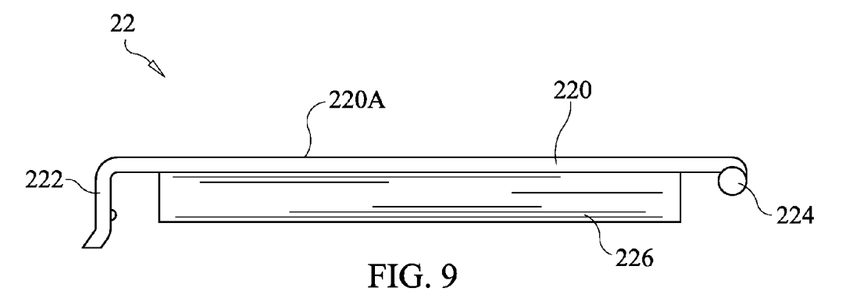
FIG. 9 is an isolated side view of the specimen cup system's lid in accordance with the system embodiment illustrated in FIG. 1.

Rim 20 is a monolithic rigid and open ring-like structure defining a tab 202 at the outside front thereof for engagement with locking tab 222 of lid 22, a hinge cavity 204 at the back thereof for engagement with hinge pin 224 of lid 22, and an inner annular ridge 206. A top side 206A of inner annular ridge 206 forms a countersunk annular ledge for engagement with annular rim region 220A when lid 22 is closed. A lower side 206B of inner annular ridge 206 defines an annular seat resting on the annular top 180 of annular seal 18 (FIG. 12). Locking tabs 208 are provided at the internal periphery of rim 20 for engagement between upper flange 14A and lower flange 14B as will be explained further below.

Annular seal 18 is a flexible monolithic and ring-like structure defining an annular U-shaped channel 182 for engagement with the top rim of sample cup 14 as shown in FIG. 12. More specifically, annular channel 182 fits over the top of sample cup 14 such that the outer portion of seal 18 comes to rest above the two spaced-apart annular flanges 14A and 14B formed around the outer perimeter of sample cup 14, while the inner portion of seal 18 extends into the top of sample cup 14.

As shown in FIG. 12, annular channel 182 of annular seal 18 fits over the top of sample cup 14 just above upper annular flange 14A. Rim 20 is configured to extend over and snap onto sample cup 14 between upper flange 14A and lower flange 14B using tabs 208 thereby capturing annular seal 18 between rim 20 and the top of sample cup 14. Note that the inner annular portion of annular seal 18 extends inside of the inner edge of annular ridge 206. In this way, annular seal 18 and annular wall 226 of lid 22 engage each other in an annular sealing fashion when lid 22 is in the closed position as shown.

In describing the operation of the present invention, reference will be made to all of the above-described views of the present invention. Prior to use of the specimen cup system of the present invention, base 12 is coupled to sample cup 14 in the pre-test position of system 10 using the above-described tab-to-slot mating, and seal 18/rim 20/lid 22 are coupled to specimen cup 140 as described above. As a result, specimen cup system 10 is a single integrated assembly even when lid 22 is open thereby simplifying its handling and use.

Specimen cup system 10 is assembled and packaged in its pre-test position, i.e., opening 126 in post 122 (of base 12) is aligned with first opening 146C of post receptacle 146 (of sample cup 14). In this way, chamber 124 in post 122 is in fluid communication with specimen cup 140 while being sealed off from test cup 142. When a body-fluid sample is deposited in specimen cup 140, chamber 124 fills with a portion of the body-fluid sample. Lid 22 is then closed thereby automatically sealing specimen cup 140 as described above. If desired, a security tape (not shown) can be applied to/over lid 22 as is known in the art.

At test time, base 12 is simply rotated to its test position, i.e., until opening 126 in post 122 is aligned with second opening 146D of post receptacle 146. Once openings 126 and 146D are aligned, the portion of the body-fluid sample in chamber 124 flows via gravity into test cup 142 where it can come into contact with the test strip(s) in test card 24. Note that during the rotation of base 12, edges 128 of opening 126 (and, if present, edges 125) seal against the inside walls of post receptacle 146 to thereby seal off specimen cup 140 and maintain any remaining body-fluid sample in specimen cup 140 in a sealed and contaminant-free state. Such rotation of base 12 will also place positioning indicia 138 and 150 in positions (e.g., on the same side of specimen cup system 10, aligned with one another, etc.) that clearly indicate that specimen cup system 10 is in its test position.

Once openings 126 and 146D are aligned, tabs 152 and 154 will reside in the wider width regions or notches 130B and 132B of slots 130 and 132 (in base 12). The bias in tabs 152 and 154 causes them to flex radially outward such that tabs 152 and 154 are captured in wider width regions 130B and 132B, respectively. That is, any attempt to rotate base 12 back to its pre-test position would cause tabs 152 and 154 to engage the corresponding lips 130C and 132C of slots 130 and 132. In this way, base 12 is locked in the test position and is prevented from rotation back to the system's pre-test position (i.e., where opening 126 is aligned with opening 146C).

With base 12 locked in the test position, the remaining portion of the body-fluid sample in specimen cup 140 cannot be accessed unless lid 22 is removed. As a result, once specimen cup system 10 has been placed in the test position, the remaining body-fluid sample in specimen cup 140 is guaranteed to be in a sealed and contaminant-free environment as long as lid 22 is not removed/broken. Accordingly, the present invention guarantees the trustworthiness of any follow-up testing on the remaining body-fluid sample. In addition, because test card 24 is sealed in place during the manufacture of system 10, test card 24 is tamperproof thereby assuring that the test card positioned during manufacturing is the test card used at test time and the one that remains there post-testing. Thus, the system of the present invention provides a high degree of confidence in test results for both the test subject and the testing entity. The sample cup's unique sealing arrangement makes it easy for a test subject to fill and seal the sample cup as the integrated system incorporates lid, sealing and testing features to eliminate the handling of multiple parts.

Although the invention has been described relative to a specific embodiment thereof, there are numerous variations and modifications that will be readily apparent to those skilled in the art in light of the above teachings. It is therefore to be understood that the invention may be practiced other than as specifically described.

What is claimed as new and desired to be secured by Letters Patent of the United States is:

The invention claimed is:

1. A specimen cup system for sample testing, comprising:
   a cup defining a first reservoir and a second reservoir wherein said first reservoir and said second reservoir are in fluid communication with one another at a lower portion of said cup, said first reservoir having an open top and having an upper annular flange and a lower annular flange defined at an external periphery of said open top, said upper annular flange and said lower annular flange being spaced apart from one another, said second reservoir being sealed except for said fluid communication with said first reservoir;
   a specimen test card permanently disposed in said second reservoir;
   a base rotatably coupled to said lower portion of said cup, said base defining a chamber having an opening therein, said base rotatable from a first position to a second position relative to said cup wherein said opening of said chamber is in fluid communication only with said first reservoir when said base is in said first position, wherein said opening of said chamber is in fluid communication only with said second reservoir when said base is in said second position, and wherein said base and said cup are locked together to prevent relative rotation when said base is in said second position;
   a ring-like flexible seal defining a channel fitted over said open top wherein said upper annular flange and said lower annular flange are exposed;
   a ring-like open rim fitted over said seal, said rim having tabs captured between said upper annular flange and said lower annular flange wherein said seal is captured between said open top and said rim, and wherein an annular portion of said seal is exposed inside of said open top; and
   a solid lid hingedly coupled to said rim, said lid including an annular wall extending therefrom, said annular wall sized to pass through said rim and to sealingly engage said annular portion of said seal when said lid is hingedly positioned to be fully engaged with said rim.

2. A specimen cup system as in claim 1, wherein said cup is made from a transparent material.

3. A specimen cup system as in claim 1, wherein said lid includes a locking tab for locking onto said rim when said lid is fully engaged with said rim.

4. A specimen cup system as in claim 1,
   wherein said annular wall of said lid lies within an outer periphery of said lid wherein an annular rim of said lid is defined about said annular wall,
   wherein said rim further defines a countersunk annular ledge, and
   wherein, when said lid is fully engaged with said lid, said annular rim rests on said countersunk annular ledge.

5. A specimen cup system for sample testing, comprising:
   a cup defining a first reservoir and a second reservoir wherein said first reservoir and said second reservoir are in fluid communication with one another at a lower portion of said cup, said first reservoir having an open top and having an upper annular flange and a lower annular flange defined at an external periphery of said open top, said upper annular flange and said lower annular flange being spaced apart from one another, said second reservoir being sealed except for said fluid communication with said first reservoir;
   a specimen test card permanently disposed in said second reservoir;
   a cylindrical receptacle formed at a bottom of said first reservoir and extending vertically therein, said receptacle having (i) a first opening defined at said bottom of said first reservoir, (ii) a second opening in a radial wall of said receptacle for fluid communication with said first reservoir, and (iii) a third opening in said radial wall of said receptacle for fluid communication with said second reservoir;
   a base having a hollow post extending vertically therefrom for insertion in said first opening of said receptacle, said hollow post having a radial opening formed therein that, when aligned with said second opening, defines a pretest condition, said hollow post forming a fluid tight seal with said receptacle about said radial opening;
an arrangement of tabs coupled to and extending from said bottom of said first reservoir;
an arrangement of slots formed in said base in correspondence with said arrangement of tabs, wherein said base is coupled to said bottom of said cup in a rotatable fashion by engagement of said tabs with said slots and wherein said hollow post can be rotated to align said radial opening with said third opening to define a test condition;
a ring-like flexible seal defining a channel fitted over said open top of said first reservoir wherein said upper annular flange and said lower annular flange are exposed;
a ring-like open rim fitted over said seal, said rim having tabs captured between said upper annular flange and said lower annular flange wherein said seal is captured between said open top and said rim, and wherein an annular portion of said seal is exposed inside of said open top; and
a solid lid hingedly coupled to said rim, said lid including an annular wall extending therefrom, said annular wall sized to pass through said rim and to sealingly engage said annular portion of said seal when said lid is hingedly positioned to be fully engaged with said rim.

6. A specimen cup system as in claim 5, further comprising first indicia on said cup and second indicia on said base wherein one of said pre-test condition and said test condition are indicated by a location of said first indicia relative to a location of said second indicia.

7. A specimen cup system as in claim 5, wherein two of said tabs are lipped tabs disposed about said first opening at diametrically opposed locations, said lipped tabs being biased away from one another.

8. A specimen cup system as in claim 7, wherein each of said slots engaging said lipped tabs is configured to prevent further rotation of said hollow post once said test condition is so-defined.

9. A specimen cup system as in claim 5 wherein, when said base is coupled to said bottom of said cup and said base is adapted to rest on a planar surface, said open top of said first reservoir defines a plane that is non-parallel with respect to the planar surface.

10. A specimen cup system as in claim 5, wherein said cup is made from a transparent material.

11. A specimen cup system as in claim 5, wherein said lid includes a locking tab for locking onto said rim when said lid is fully engaged with said rim.

12. A specimen cup system as in claim 5,
wherein said annular wall of said lid lies within an outer periphery of said lid wherein an annular rim of said lid is defined about said annular wall,
wherein said rim further defines a countersunk annular ledge, and
wherein, when said lid is fully engaged with said lid, said annular rim rests on said countersunk annular ledge.

* * * * *